United States Patent
Greene, Jr. et al.

(10) Patent No.: US 6,238,403 B1
(45) Date of Patent: May 29, 2001

(54) FILAMENTOUS EMBOLIC DEVICE WITH EXPANSIBLE ELEMENTS

(75) Inventors: George R. Greene, Jr., Costa Mesa; Robert F. Rosenbluth; Brian J. Cox, both of Laguna Niguel, all of CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

(21) Appl. No.: 09/410,970

(22) Filed: Oct. 4, 1999

(51) Int. Cl.$^7$ ................................................ A61F 11/00

(52) U.S. Cl. ............................................... 606/108

(58) Field of Search .................... 606/108, 191, 606/194, 195, 200

(56) References Cited

U.S. PATENT DOCUMENTS

| | | |
|---|---|---|
| 3,709,842 | 1/1973 | Stoy et al. . |
| 4,301,803 | * 11/1981 | Handa et al. ........................ 128/349 |
| 4,365,621 | 12/1982 | Brundin . |

(List continued on next page.)

FOREIGN PATENT DOCUMENTS

| | | |
|---|---|---|
| WO99/23954 | 5/1999 | (WO) . |
| WO99/56783 | 11/1999 | (WO) . |

OTHER PUBLICATIONS

Chirila, T.V. et al., "Poly(2–hydroxyethyl methacrylate) sponges as implant material: in vivo and in vitro evaluation of cellular invasion," *Biomaterials*, 1993, vol. 14 No. 1
Horàk, D. et al., "Hydrogels in endovascular embolization.II, Clinical use of spherical particles," *Biomaterials* (1986), vol. 7, Nov., pp. 467–470.
Horàk, D. et al., "New radiopaque polyHEMA–based hydrogel particles," *Journal of Biomedical Materials Research*, vol. 34, pp. 183–188 (1997).
Latchaw, R.E., M.D. et al.., "Polyvinyl Foam Embolization of Vascular and Neoplastic Lesions of the Head, Neck, and Spine," Department of Radiology, University of Minnesota Hospitals, Radiology 131:669–679, Jun. 1979.

(List continued on next page.)

*Primary Examiner*—Gene Mancene
*Assistant Examiner*—Eduardo C. Robert
(74) *Attorney, Agent, or Firm*—Klein & Szekeres, LLP

(57) ABSTRACT

An embolization device includes a plurality of highly-expansible embolizing elements disposed at spaced intervals along a filamentous carrier. In a preferred embodiment, the carrier is a suitable length of very thin, highly flexible filament of nickel/titanium alloy. The embolizing elements are separated from each other on the carrier by radiopaque spacers in the form of highly flexible microcoils made of platinum or platinum/tungsten alloy. In a preferred embodiment, the embolizing elements are made of a hydrophilic, macroporous, polymeric, hydrogel foam material. The device is particularly suited for embolizing a vascular site such as an aneurysm. The embolization bodies have an initial configuration in the form of small, substantially cylindrical "micropellets" of small enough outside diameter to fit within a microcatheter. The bodies are hydrophilically expansible into an expanded configuration in which they substantially conform to and fill the vascular site while connected to the carrier. A method for embolizing a vascular site using this device includes the steps of: (a) passing a microcatheter intravascularly so that its distal end is in a vascular site; (b) providing a vascular embolization device comprising a plurality of highly expansible embolizing elements carried on a filamentous carrier and separated from each other on the carrier by microcoil spacers; (c) passing the embolization device through the microcatheter so that it emerges from the distal end of the microcatheter into the vascular site; and (d) expanding the embolizing elements in situ substantially to fill the vascular site.

26 Claims, 4 Drawing Sheets

U.S. PATENT DOCUMENTS

| | | | | |
|---|---|---|---|---|
| 4,402,319 | * | 9/1983 | Handa et al. | 128/325 |
| 4,509,504 | | 4/1985 | Brundin . | |
| 4,529,739 | | 7/1985 | Scott et al. . | |
| 4,663,358 | | 5/1987 | Hyon et al. . | |
| 5,120,349 | | 6/1992 | Stewart et al. . | |
| 5,129,180 | | 7/1992 | Stewart et al. . | |
| 5,226,911 | | 7/1993 | Chee et al. . | |
| 5,258,042 | | 11/1993 | Mehta . | |
| 5,304,194 | | 4/1994 | Chee et al. . | |
| 5,350,397 | | 9/1994 | Palermo et al. . | |
| 5,354,290 | | 10/1994 | Gross . | |
| 5,456,693 | | 10/1995 | Conston et al. . | |
| 5,541,234 | | 7/1996 | Unger et al. . | |
| 5,573,994 | | 11/1996 | Kabra et al. . | |
| 5,582,619 | * | 12/1996 | Ken | 606/191 |
| 5,624,685 | | 4/1997 | Takahashi et al. . | |
| 5,645,558 | | 7/1997 | Horton . | |
| 5,672,634 | | 9/1997 | Tseng et al. . | |
| 5,750,585 | | 5/1998 | Park et al. . | |
| 5,752,974 | | 5/1998 | Rhee et al. . | |
| 5,766,160 | * | 6/1998 | Samson et al. | 606/108 |
| 5,766,219 | | 6/1998 | Horton . | |
| 5,823,198 | | 10/1998 | Jones et al. . | |
| 5,891,155 | | 4/1999 | Irie . | |
| 5,980,514 | * | 11/1999 | Kupiecki et al. | 606/108 |
| 6,066,149 | * | 5/2000 | Samson et al. | 606/159 |
| 6,093,199 | * | 7/2000 | Brown et al. | 606/200 |

OTHER PUBLICATIONS

Vacanti et al., "Tissue Engineering: The Design and Fabrication of Living Replacement Devices for Surgical Reconstruction and Transplanatation." *The Lancet* (vol. 354, Supplement 1) pp. 32–34 (Jul., 1999).

Langer, "Tissue Engineering: A new Field and Its Challenges," *Pharmaceutical Research*, vol. 14, No. 7, pp. 840–841 (Jul., 1997).

Persidis, "Tissue Engineering," *Nature Biotechnolgy*, vol. 17, pp. 508–510 (May, 1999).

Zollikofer, Christoph et al., "A Combination of Stainless Steel Coil and Compressed Ivalon: A New Technique for Embolization of Large Arteries and Arteriovenous Fistulas", *Technica Notes*, vol. 138, pp. 229–231, Jan. 1981.

Hogg, Phillip J. et al., "Interaction of platelet–derived growth factor with thrombospondin I", *Biochem J.* (1997) 326, 709–716.

Larsen, Nancy E. et al., "Hyland gel compositions for percutaneous embolization", *Journal of Biomedical Materials Research*, vol. 25, 699–710 (1991).

Soranzo, C. et al., "Evaluation of Two Hyaluronan Derivatives (Hyaff7 and ACP Sponges) For Bone Healing", *The 20 th Annual Meeting of the Society for Biomaterials*, Apr. 5–9, 1994, p. 99.

Hoekstra, Djoerd, "Hyaluronan–Modified Surfaces for Medical Devices", *Medical Device & Diagnostic Industry*, Feb. 1999, pp. 48–56.

Woerly, S. et al., "Intracerebral Implantation of Hydrogel–Coupled Adhesion Peptides: Tissue Reaction", *Jouranl of Neural Transplantation & Plasticity*, vol. 5, No. 4, 1995, pp. 245–255.

Edelman, Elazer R., "Controlled and modulated release of basic fibroblast growth factor", *Biomaterials*, Sep. 1991, vol. 12, pp. 619–626.

Tadavarthy, S. Murthy et al., "Polyvinyl Alcohol (Ivalon)—A New Embolic Material," Department of Radiology, University of Minnesota Hospitals, vol. 125, No. 3, Nov. 1975.

Zollikofer, Christoph et al., "Therapeutic Blockade of Arteries Using Compressed Ivalon[1]", Department of Radiology University of Minnesota Hospitals, Radiology 136:635–640, Sep., 1980).

* cited by examiner

FILAMENTOUS EMBOLIC DEVICE WITH EXPANSIBLE ELEMENTS

CROSS REFERENCE TO RELATED APPLICATION

Not Applicable

FEDERALLY SPONSORED RESEARCH OR DEVELOPMENT

Not applicable

BACKGROUND OF THE INVENTION

The present invention relates to the field of methods and devices for the embolization of vascular aneurysms and similar vascular abnormalities. More specifically, the present invention relates to an embolic device that is inserted into a vascular site such as an aneurysm to create an embolism therein and a method for embolizing a vascular site using the device.

The embolization of blood vessels is desired in a number of clinical situations. For example, vascular embolization has been used to control vascular bleeding, to occlude the blood supply to tumors, and to occlude vascular aneurysms, particularly intracranial aneurysms. In recent years, vascular embolization for the treatment of aneurysms has received much attention. Several different treatment modalities have been employed in the prior art. U.S. Pat. No. 4,819,637— Dormandy, Jr. et al., for example, describes a vascular embolization system that employs a detachable balloon delivered to the aneurysm site by an intravascular catheter. The balloon is carried into the aneurysm at the tip of the catheter, and it is inflated inside the aneurysm with a solidifying fluid (typically a polymerizable resin or gel) to occlude the aneurysm. The balloon is then detached from the catheter by gentle traction on the catheter. While the balloon-type embolization device can provide an effective occlusion of many types of aneurysms, it is difficult to retrieve or move after the solidifying fluid sets, and it is difficult to visualize unless it is filled with a contrast material. Furthermore, there are risks of balloon rupture during inflation and of premature detachment of the balloon from the catheter.

Another approach is the direct injection of a liquid polymer embolic agent into the vascular site to be occluded. One type of liquid polymer used in the direct injection technique is a rapidly polymerizing liquid, such as a cyanoacrylate resin, particularly isobutyl cyanoacrylate, that is delivered to the target site as a liquid, and then is polymerized in situ. Alternatively, a liquid polymer that is precipitated at the target site from a carrier solution has been used. An example of this type of embolic agent is a cellulose acetate polymer mixed with bismuth trioxide and dissolved in dimethyl sulfoxide (DMSO). Another type is ethylene vinyl alcohol dissolved in DMSO. On contact with blood, the DMSO diffuses out, and the polymer precipitates out and rapidly hardens into an embolic mass that conforms to the shape of the aneurysm. Other examples of materials used in this "direct injection" method are disclosed in the following U.S. Pat. No. : 4,551,132—Pasztor et al.; U.S. Pat. No. 4,795,741—Leshchiner et al.; U.S. Pat. No. 5,525,334—Ito et al.; and U.S. Pat. No. 5,580,568—Gieffet al.

The direct injection of liquid polymer embolic agents has proven difficult in practice. For example, migration of the polymeric material from the aneurysm and into the adjacent blood vessel has presented a problem. In addition, visualization of the embolization material requires that a contrasting agent be mixed with it, and selecting embolization materials and contrasting agents that are mutually compatible may result in performance compromises that are less than optimal. Furthermore, precise control of the deployment of the polymeric embolization material is difficult, leading to the risk of improper placement and/or premature solidification of the material. Moreover, once the embolization material is deployed and solidified, it is difficult to move or retrieve.

Another approach that has shown promise is the use of thrombogenic microcoils. These microcoils may be made of a biocompatible metal alloy (typically platinum and tungsten) or a suitable polymer. If made of metal, the coil may be provided with Dacron fibers to increase thrombogenicity. The coil is deployed through a microcatheter to the vascular site. Examples of microcoils are disclosed in the following U.S. Pat. No. : 4,994,069—Ritchart et al.; U.S. Pat. No. 5,133,731—Butler et al.; U.S. Pat. No. 5,226,911—Chee et al.; U.S. Pat. No. 5,312,415—Palermo; U.S. Pat. No. 5,382,259—Phelps et al.; U.S. Pat. No. 5,382,260—Dormandy, Jr. et al.; U.S. Pat. No. 5,476,472—Dormandy, Jr. et al.; U.S. Pat. No. 5,578,074—Mirigian; U.S. Pat. No. 5,582,619—Ken; U.S. Pat. No. 5,624,461—Mariant; U.S. Pat. No. 5,645,558—Horton; U.S. Pat. No. 5,658,308—Snyder; and U.S. Pat. No. 5,718,711—Berenstein et al.

The microcoil approach has met with some success in treating small aneurysms with narrow necks, but the coil must be tightly packed into the aneurysm to avoid shifting that can lead to recanalization. Microcoils have been less successful in the treatment of larger aneurysms, especially those with relatively wide necks. A disadvantage of microcoils is that they are not easily retrievable; if a coil migrates out of the aneurysm, a second procedure to retrieve it and move it back into place is necessary. Furthermore, complete packing of an aneurysm using microcoils can be difficult to achieve in practice.

A specific type of microcoil that has achieved a measure of success is the Guglielmi Detachable Coil ("GDC"). The GDC employs a platinum wire coil fixed to a stainless steel delivery wire by a solder connection. After the coil is placed inside an aneurysm, an electrical current is applied to the delivery wire which heats sufficiently to melt the solder junction, thereby detaching the coil from the guidewire. The application of the current also creates a positive electrical charge on the coil, which attracts negatively-charged blood cells, platelets, and fibrinogen, thereby increasing the thrombogenicity of the coil. Several coils of different diameters and lengths can be packed into an aneurysm until the aneurysm is completely filled. The coils thus create and hold a thrombus within the aneurysm, inhibiting its displacement and its fragmentation.

The advantages of the GDC procedure are the ability to withdraw and relocate the coil if it migrates from its desired location, and the enhanced ability to promote the formation of a stable thrombus within the aneurysm. Nevertheless, as in conventional microcoil techniques, the successful use of the GDC procedure has been substantially limited to small aneurysms with narrow necks.

Still another approach to the embolization of an abnormal vascular site is the injection into the site of a biocompatible hydrogel, such as poly (2-hydroxyethyl methacrylate) ("pHEMA" or "PHEMA"); or a polyvinyl alcohol foam ("PAF"). See, e.g., Horák et al., "Hydrogels in Endovascular Embolization. II. Clinical Use of Spherical Particles", *Biomaterials*, Vol. 7, pp. 467–470 (Nov., 1986); Rao et al., "Hydrolysed Microspheres from Cross-Linked Polymethyl Methacrylate", *J. Neuroradiol.*, Vol. 18, pp. 61–69 (1991); Latchaw et al., "Polyvinyl Foam Embolization of Vascular and Neoplastic Lesions of the Head, Neck, and Spine", *Radiology*, Vol. 131, pp. 669–679 (June, 1979). These materials are delivered as microparticles in a carrier fluid that is injected into the vascular site, a process that has proven difficult to control.

A further development has been the formulation of the hydrogel materials into a preformed implant or plug that is installed in the vascular site by means such as a microcatheter. See, e.g., U.S. Pat. No. 5,258,042—Mehta. These types of plugs or implants are primarily designed for obstructing blood flow through a tubular vessel or the neck of an aneurysm, and they are not easily adapted for precise implantation within a sac-shaped vascular structure, such as an aneurysm, so as to fill substantially the entire volume of the structure.

U.S. Pat. No. 5,823,198—Jones et al. discloses an expansible PVA foam plug that is delivered to the interior of an aneurysm at the end of a guidewire. The plug comprises a plurality of pellets or particles that expand into an open-celled structure upon exposure to the fluids within the aneurysm so as to embolize the aneurysm. The pellets are coated with a blood-soluble restraining agent to maintain them in a compressed state and attached to the guidewire until delivered to the aneurysm. Because there is no mechanical connection between the pellets and the guidewire (other than the relatively weak temporary bond provided by the restraining agent), however, premature release and migration of some of the pellets remains a possibility.

There has thus been a long-felt, but as yet unsatisfied need for an aneurysm treatment device and method that can substantially fill aneurysms of a large range of sizes, configurations, and neck widths with a thrombogenic medium with a minimal it risk of inadvertent aneurysm rupture or blood vessel wall damage. There has been a further need for such a method and device that also allow for the precise locational deployment of the medium, while also minimizing the potential for migration away from the target location. In addition, a method and device meeting these criteria should also be relatively easy to use in a clinical setting. Such ease of use, for example, should preferably include a provision for good visualization of the device during and after deployment in an aneurysm.

SUMMARY OF THE INVENTION

Broadly, an embolization device, according to a first aspect of the present invention, comprises a plurality of highly-expansible embolizing elements non-releaseably connected to a flexible filamentous carrier at spaced intervals along the length of the carrier. In a preferred embodiment, the carrier is a suitable length of very thin, highly flexible filament of nickel/titanium alloy. The embolizing elements are separated from each other on the carrier by radiopaque spacers in the form of highly flexible microcoils made of platinum or platinum/tungsten alloy, as in the thrombogenic microcoils of the prior art, as described above.

In a preferred embodiment, the embolizing elements are made of a hydrophilic, macroporous, polymeric, hydrogel foam material, in particular a water-swellable foam matrix formed as a macroporous solid comprising a foam stabilizing agent and a polymer or copolymer of a free radical polymerizable hydrophilic olefin monomer cross-linked with up to about 10% by weight of a multiolefin-functional cross-linking agent. Such a material is described in U.S. Pat. No. 5,750,585—Park et al., the disclosure of which is incorporated herein by reference. The material may be modified, or provided with additives, to make the implant visible by conventional imaging techniques.

A second aspect of the present invention is a method for embolizing a vascular site, comprising the steps of: (a) passing a microcatheter intravascularly so that its distal end is in a vascular site; (b) providing a vascular embolization device comprising a plurality of highly expansible embolizing elements carried on a filamentous carrier and separated from each other on the carrier by microcoil spacers; (c) passing the embolization device through the microcatheter so that it emerges from the distal end of the microcatheter into the vascular site; and (d) expanding the embolizing elements in situ substantially to fill the vascular site.

The embolization bodies, in the preferred embodiment, have an initial configuration in the form of small, substantially cylindrical "micropellets" of small enough outside diameter to fit within the microcatheter. The bodies are hydrophilically expansible into an expanded configuration in which they substantially conform to and fill the vascular site.

The present invention provides a number of significant advantages. Specifically, the present invention provides an effective vascular embolization device that can be deployed within a vascular site with excellent locational control, and with a lower risk of vascular rupture, tissue damage, or migration than with prior art devices. Furthermore, the embolization device effects a conformal fit within the site that promotes effective embolization, and yet its ability to be delivered to the site through a microcatheter facilitates precise and highly controllable deployment. In addition, the essentially filamentous initial configuration of the embolization device, whereby it readily conforms to the interior dimensions of the vascular site, allows it to be used effectively to embolize vascular sites having a wide variety of sizes, configurations, and (in the particular case of aneurysms) neck widths. These and other advantages will be readily appreciated from the detailed description that follows.

DETAILED DESCRIPTION OF THE INVENTION

Figure 1:
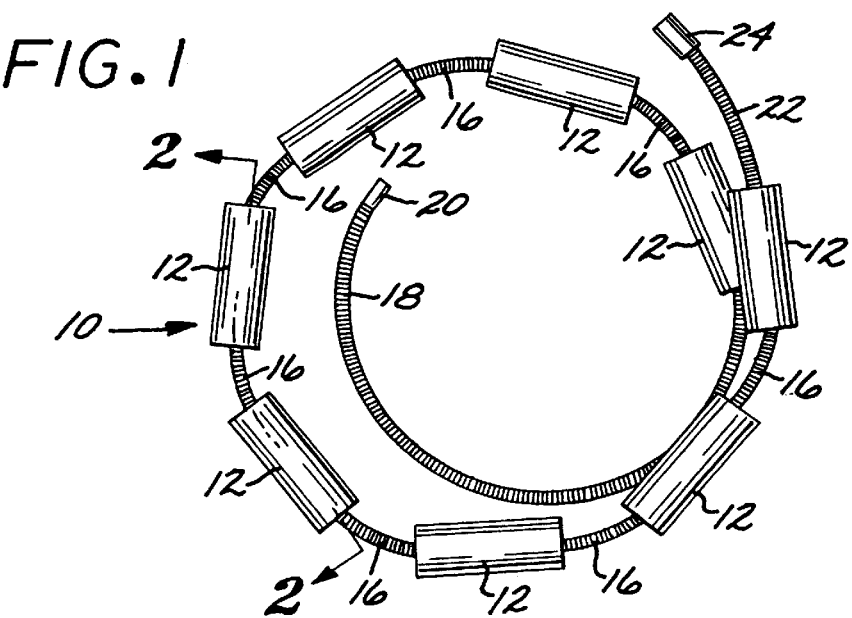
FIG. 1 is an elevational view of a vascular embolization device in accordance with a preferred embodiment of the invention.
Figure 2:
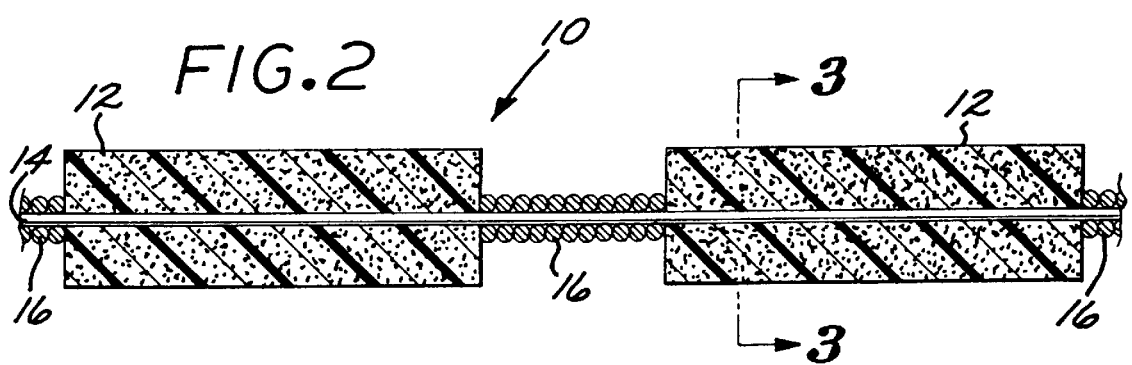
FIG. 2 is a cross-sectional view taken along line 2—2 of FIG. 1.
Figure 3:
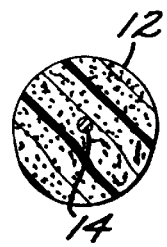
FIG. 3 is a cross-sectional view taken along line 3—3 of FIG. 2.

The Embolization Device. A vascular embolization device 10, in accordance with the present invention, is shown in FIGS. 1, 2 and 3. In the preferred embodiment, the embolization device 10 comprises a plurality of embolizing bodies, each configured as a substantially cylindrical "micropellet" 12, located at spaced intervals along a filamentous carrier 14. The number of micropellets 12 will vary, depending on the length of the carrier 14, which, turn, will depend on the size of the vascular site to be embolized. For a large vascular site, for example, eight to twelve micropellets may be used, although an even larger number may be used if necessary. In some applications (e.g., very small aneurysms), as few as one or two micropellets may be used.

Also carried on the carrier 14 is a plurality of highly flexible microcoil spacers 16, each of which is disposed between and separates a pair of micropellets 12. The carrier 14 has a distal portion on which is carried a relatively long distal microcoil segment 18 that is retained in place by a distal retention member 20. The carrier 14 has a proximal portion on which is carried a relatively long proximal microcoil segment 22. The proximal end of the device 10 is terminated by a hydrogel linkage element 24, to be described below. The spacers 16, the distal microcoil segment 18, and the proximal microcoil segment 22 are all highly flexible, and they are it preferably made of platinum or platinum/tungsten wire, which has the advantages of being biocompatible and radiopaque. The micropellets 12 may be fixed in place on the filamentous carrier 14 (e.g., by a suitable biocompatible, water-insoluble adhesive), or they may be simply strung loosely on the carrier 14 between successive spacers 16.

The micropellets 12 are preferably formed of a biocompatible, macroporous, hydrophilic hydrogel foam material, in particular a water-swellable foam matrix formed as a macroporous solid comprising a foam stabilizing agent and a polymer or copolymer of a free radical polymerizable hydrophilic olefin monomer crosslinked with up to about 10% by weight of a multiolefin-functional cross-linking agent. A suitable material of this type is described in U.S. Pat. No. 5,570,585—Park et al., the disclosure of which is incorporated herein by reference.

Another suitable material for the micropellets 12 is a porous hydrated polyvinyl alcohol (PVA) foam gel prepared from a polyvinyl alcohol solution in a mixed solvent consisting of water and a water-miscible organic solvent, as described, for example, in U.S. Pat. No. 4,663,358—Hyon et al., the disclosure of which is incorporated herein by reference. Other suitable forms of PVA are described in U.S. Pat. No. 5,823,198—Jones et al. and U.S. Pat. No. 5,258,042—Mehta, the disclosures of which are incorporated herein by reference. Another suitable material is a collagen foam, of the type described in U.S. Pat. No. 5,456,693—Conston et al., the disclosure of which is incorporated herein by reference. Still another suitable material is PHEMA, as discussed in the references cited above. See, e.g., Horák et al., supra, and Rao et al., supra.

The preferred foam material, as described in the above-referenced patent to Park et al., has a void ratio of at least about 90%, and its hydrophilic properties are such that it has a water content of at least about 90% when fully hydrated. In the preferred embodiment, each of the embolizing micropellets 12 has an initial diameter of not more than about 0.5 mm prior to expansion in situ, with an expanded diameter of at least about 3 mm. To achieve such a small initial size, the micropellets 12 may be compressed to the desired size from a significantly larger initial configuration. The compression is performed by squeezing or crimping the micropellets 12 in a suitable implement or fixture, and then "setting" them in the compressed configuration by heating and/or drying.

Each of the micropellets 12 is swellable or expansible to many times (at least about 25 times, preferably at least about 70 times, and up to about 100 times) its initial (compressed) volume, primarily by the hydrophilic absorption of water molecules from an aqueous solution (e.g., resident blood plasma and/or injected saline solution), and secondarily by the filling of its pores with blood. Also, the micropellets 12 may be coated with a water-soluble coating (not shown), such as a starch, to provide a time delayed expansion. Another alternative is to coat the micropellets 12 with a temperature-sensitive coating that disintegrates in response to normal human body temperature. See, e.g., U.S. Pat. No. 5,120,349—Stewart et al. and U.S. Pat. No. 5,129,180—Stewart.

The foam material of the embolizing micropellet 12 may advantageously be modified, or provided with additives, to make the device 10 visible by conventional imaging techniques. For example, the foam can be impregnated with a water insoluble radiopaque material such as barium sulfate, as described by Thanoo et al., "Radiopaque Hydrogel Microspheres", *J. Microencapsulation*, Vol. 6, No. 2, pp. 233–244 (1989). Alternatively, the hydrogel monomers can be copolymerized with radiopaque materials, as described in Horak et al., "New Radiopaque PolyHEMA-Based Hydrogel Particles", *J. Biomedical Materials Research*, Vol. 34, pp. 183–188 (1997).

The micropellets 12 may optionally include bioactive or therapeutic agents to promote thrombosis, cellular ingrowth, and/or epithelialization. See, e.g, Vacanti et al., "Tissue Engineering: The Design and Fabrication of Living Replacement Devices for Surgical Reconstruction and Transplantation," *The Lancet*(Vol. 354, Supplement 1), pp. 32–34 (July, 1999); Langer, "Tissue Engineering: A New Field and Its Challenges," *Pharmaceutical Research*, Vol. 14., No. 7, pp. 840–841 (July, 1997); Persidis, "Tissue Engineering," *Nature Biotechnology*; Vol. 17, pp. 508–510 (May, 1999).

The filamentous carrier 14 is preferably a length of nickel/titanium wire, such as that marketed under the trade name "Nitinol". Wire of this alloy is highly flexible, and it has an excellent "elastic memory", whereby it can be formed into a desired shape to which it will return when it is deformed. In a preferred embodiment of the invention, the wire that forms the carrier 14 has a diameter of approximately 0.04 mm, and it is heat-treated to form a multi-looped structure that may assume a variety of three-dimensional shapes, such as a helix, a sphere, or an ovoid (as disclosed, for example, in U.S. Pat. No. 5,766,219—Horton, the disclosure of which is incorporated herein by reference). Preferably, the intermediate portion of the carrier 14 (i.e., the portion that includes the micropellets 12) and the proximal portion (that carries the proximal microcoil segment 22) are formed into loops having a diameter of approximately 6 mm, while the distal portion (that carries the distal microcoil segment 18) may have a somewhat greater diameter (e.g., approximately 8–10 mm). The carrier 14 may be formed of a single wire, or it may be formed of a cable or braided structure of several ultra-thin wires.

In another embodiment, the carrier 14 may be made of a thin filament of a suitable polymer, such as a PVA, that is formed in a looped structure. The polymer may be impregnated with a radiopaque material (e.g., barium sulfate or particles of gold, tantalum, or platinum), or it may enclose a core of nickel/titanium wire. Alternatively, the carrier 14 may be constructed as a "cable" of thin polymer fibers that includes fibers of an expansible polymer, such as polyvinyl alcohol (PVA), at spaced intervals to form the micropellets 12.

Still another alternative construction for the carrier 14 is a continuous length of microcoil. In such an embodiment, the micropellets 12 would be attached at spaced intervals along the length of the carrier 14.

Figure 8:
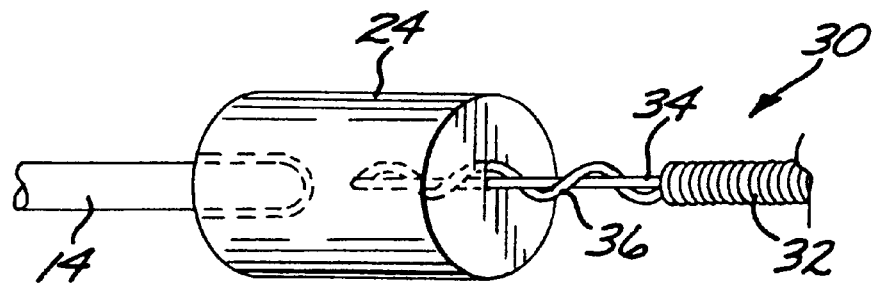
FIG. 8 is a detailed perspective view of mechanism by which the embolization device of the present invention is preferably attached to the distal end of a deployment instrument.
Figure 9:
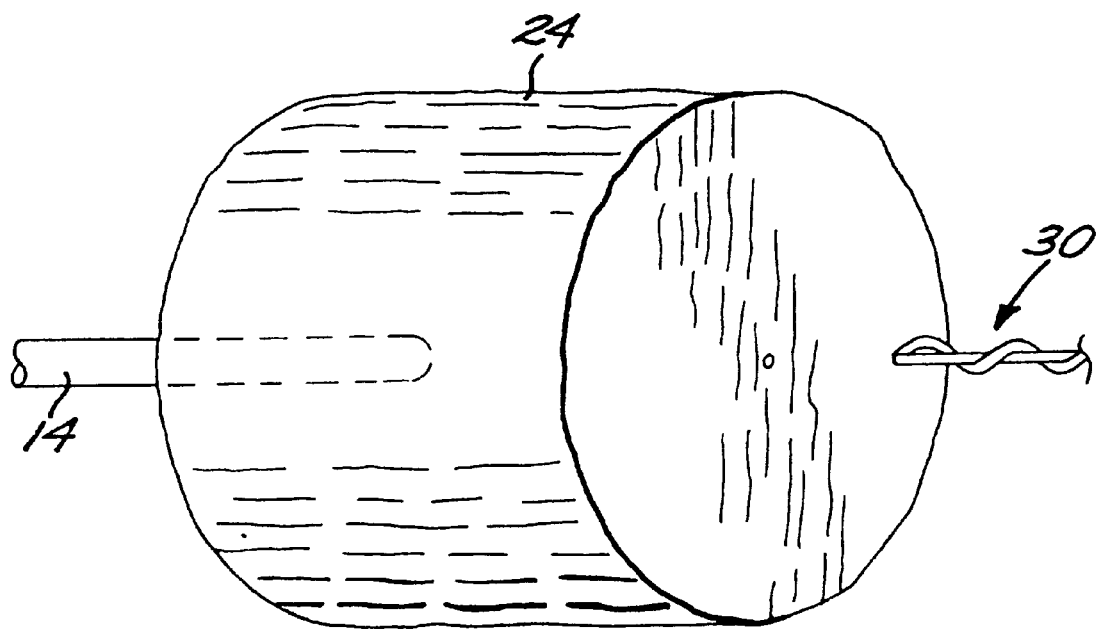
FIG. 9 is a detailed perspective view, similar to that of FIG. 8, showing the embolization device of the present invention after it has been separated from the deployment instrument.

As shown in FIGS. 1, 8, and 9, the hydrogel linkage element 24 is advantageously made of the same material as the micropellets 12. Indeed, the most proximal of the micropellets 12 may function as the linkage element 24. The linkage element 24 is attached to the proximal end of the carrier 14 by a suitable biocompatible adhesive. The purpose of the linkage element 24 is to removably attach the device 10 to a deployment instrument 30 (FIGS. 8 and 9). The deployment instrument 30 comprises a length of platinum or platinum/tungsten microcoil outer portion 32 with a flexible wire core 34 of the same or a similar metal. The deployment instrument 30 has a distal portion 36 at which the microcoil outer portion 32 has coils that are more distantly-spaced (i.e., have a greater pitch).

As shown in FIG. 8, the device 10 is initially attached to the deployment instrument 30 by means of the linkage element 24. Specifically, the linkage element 24 is installed, in a compressed state, so that it encompasses and engages both the proximal end of the embolization device 10 and the distal portion 36 of the deployment instrument 30. Thus, in the compressed state, the linkage element 24 binds the deployment instrument 30 and the embolization device 10 together. As shown in FIG. 9, and as will be described in detail below, after the device 10 is deployed in a vascular site, the linkage element 24 expands greatly, thereby loosening its grip on the distal portion 36 of the deployment instrument 30, and thus allowing the embolization device 10 to be separated from the deployment instrument 30 by pulling the latter proximally out of and away from the linkage element 24.

Figure 4:
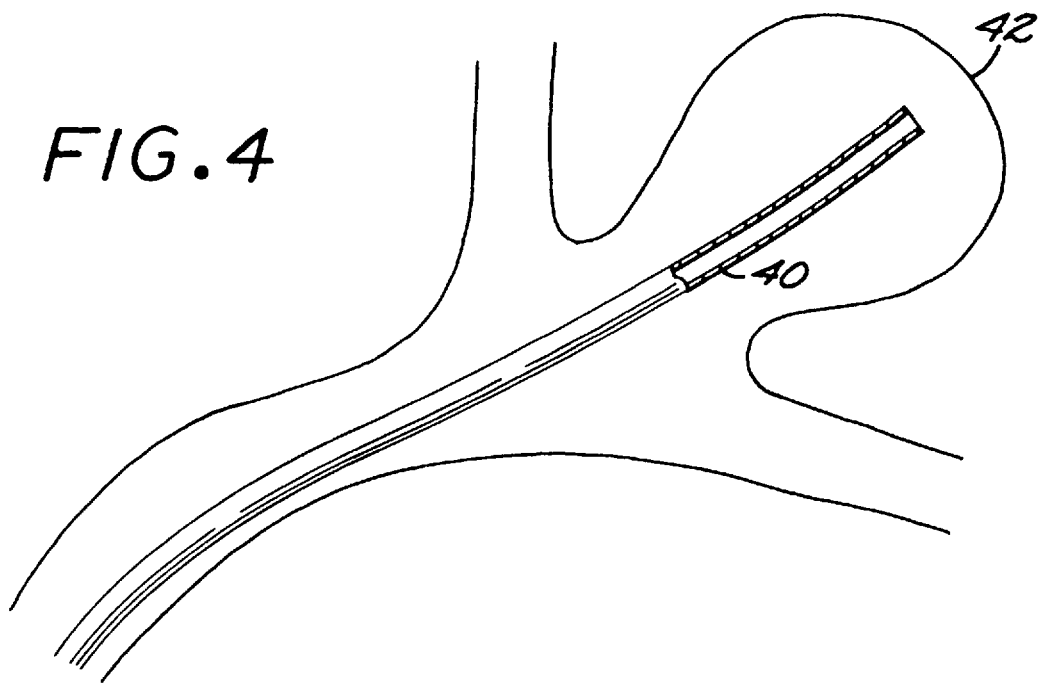
FIGS. 4 through 7 are semischematic views showing the steps in a method of embolizing a vascular site (specifically, an aneurysm) in accordance with a preferred embodiment of the embolizing method aspect of the present invention.
Figure 5:
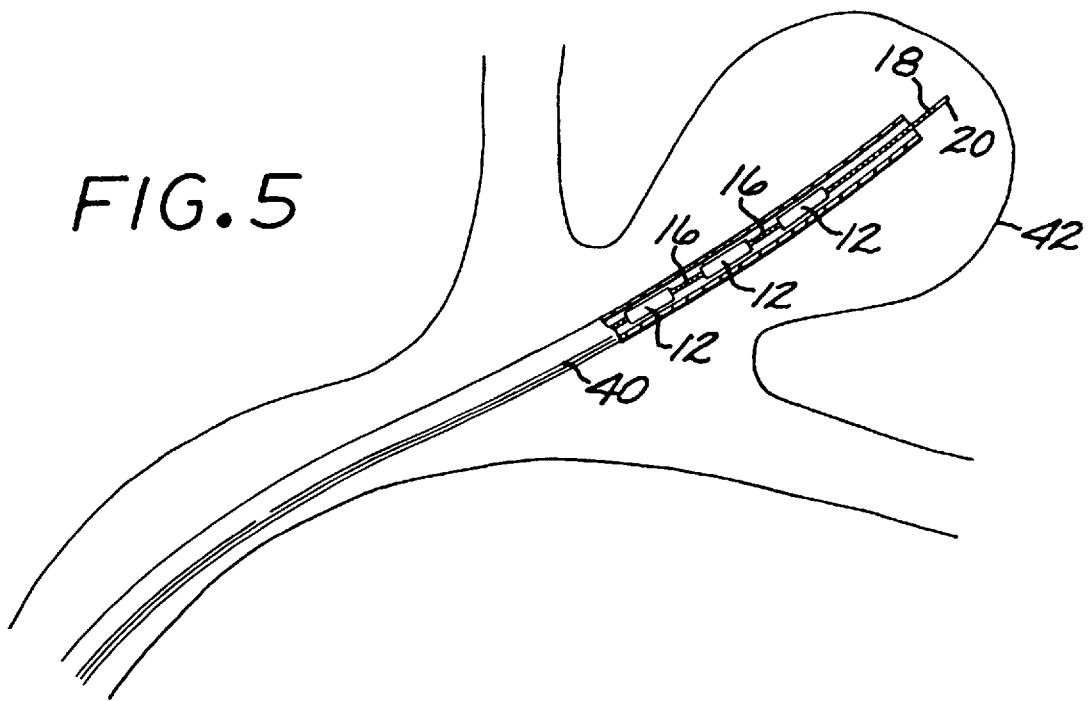
Figure 6:
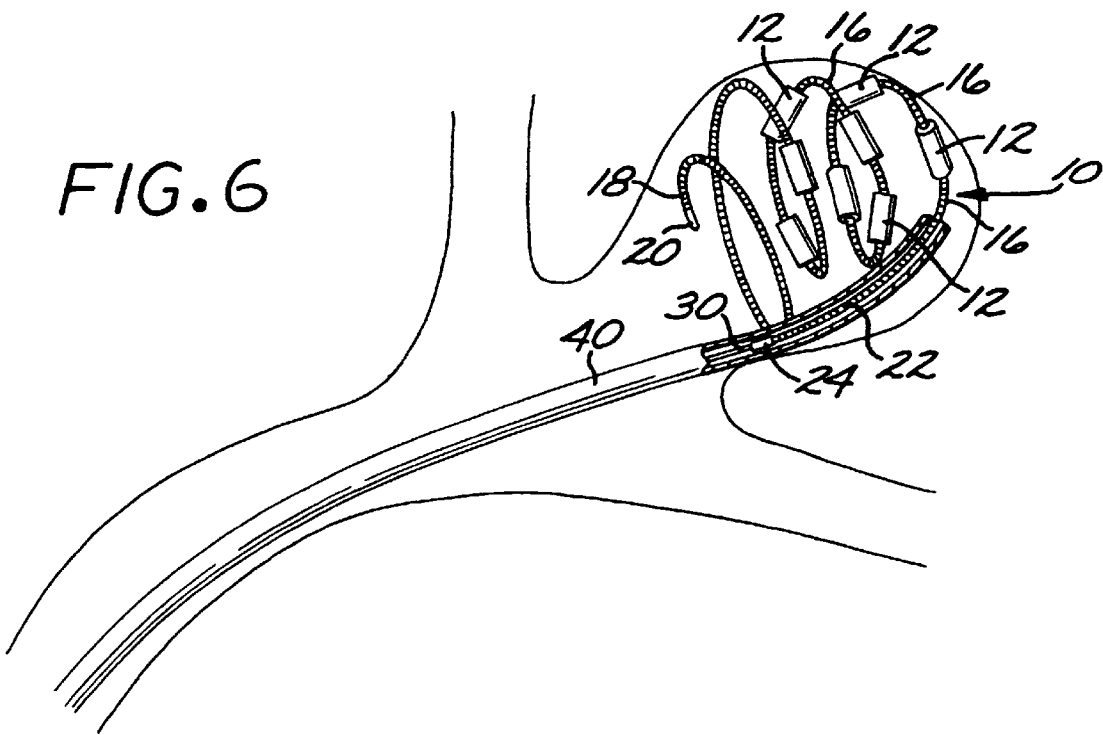

The Method for Embolizing a Vascular Site. The method of embolizing a vascular site using the embolization device 10 is illustrated in FIGS. 4 through 7. First, as shown in FIG. 4, a microcatheter 40 is threaded intravascularly, by known methods, until its distal end is located within the targeted vascular site (here, an aneurysm 42). Briefly described, this threading operation is typically performed by first introducing a catheter guidewire (not shown) along the desired microcatheter path, and then feeding the microcatheter 40 over the catheter guidewire until the microcatheter 40 is positioned adjacent the distal aspect of the dome of the aneurysm, as shown in FIG. 4. The catheter guidewire is then removed. Then, as shown in FIGS. 5 and 6, the embolization device 10, which is attached to the distal end of the deployment instrument 30, as described above, is passed axially through the microcatheter 40, using the deployment instrument 30 to push the device 10 through the microcatheter 40 until the device 10 is clear from the distal end of the microcatheter 40 and fully deployed within the aneurysm 42 (FIG. 6), filling the aneurysm from its distal aspect. The deployment procedure is facilitated by the visualization of the embolization device 10 that is readily accomplished due to its radiopaque components, as described above.

The embolization bodies or micropellets 12, in their compressed configuration, have a maximum outside diameter that is less than the inside diameter of the microcatheter 40, so that the embolization device 10 can be passed through the microcatheter 40. The micropellets 12 are preferably compressed and "set", as described above, before the device 10 is inserted into the microcatheter 40. When inserting the device 10 into the microcatheter 40, a biocompatible, substantially non-aqueous fluid, such as polyethylene glycol, may be injected into the microcatheter 40 to prevent premature expansion of the device 10 due to hydration, and to reduce friction with the interior of the microcatheter 40.

As shown in FIG. 6, when the embolization device 10 is exposed from the microcatheter 40 into the interior of the vascular site 42, the pores of the embolizing bodies or micropellets 12, and of the linkage element 22, begin to absorb aqueous fluid from the blood within the vascular site 42 to release their "set", allowing these elements to begin assuming their expanded configuration. The expansion can be enhanced and accelerated by injecting saline solution through the microcatheter 40. The expansion of the linkage element 24 allows the embolization device 10 to be separated from the deployment instrument 30, as described above, and the deployment instrument 30 can then be removed. Also, the elastic memory of the carrier 14 causes it to resume its original looped configuration once it is released from the confines of the microcatheter 40. Thus, almost immediately upon its release into the vascular site (aneurysm) 42, the embolization device begins to occupy a significant portion of the volume of the aneurysm 42.

Figure 7:
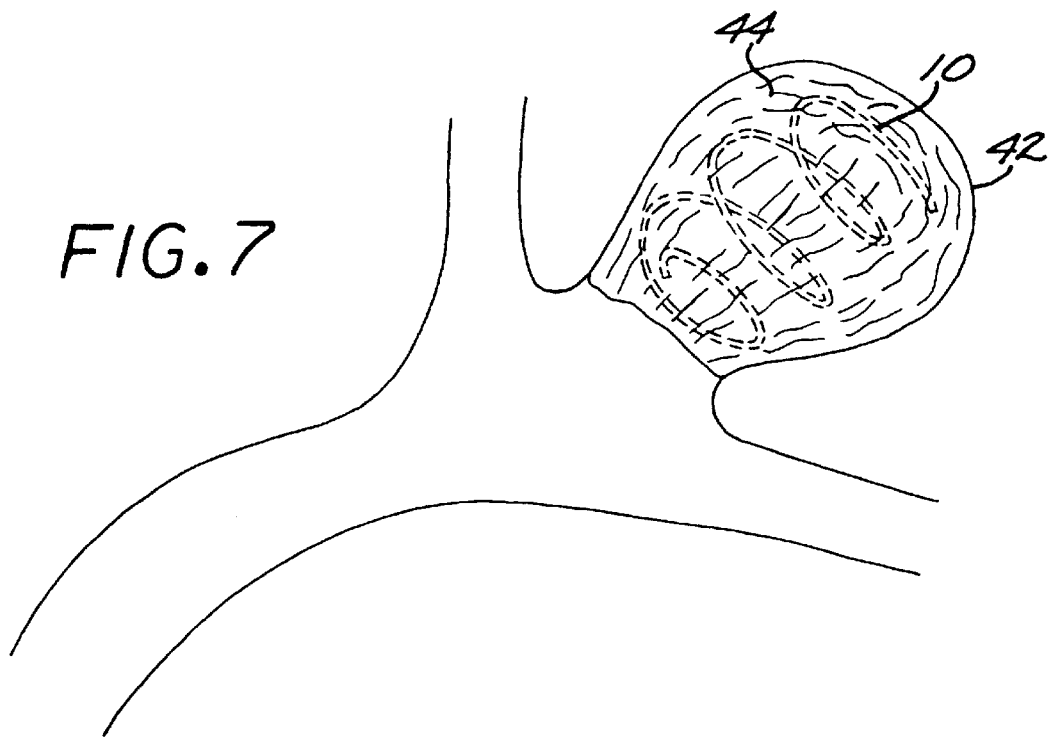

If the micropellets 12 are of a hydrophilic material, they then continue to expand in situ due to hydrophilic hydration of the material, as well as from the filling of their pores with blood. If the embolizing bodies 12 are of a non-hydrophilic material, their expansion is due to the latter mechanism only. In either case, the result, as shown in FIG. 7, the substantially complete filling of the interior of the aneurysm 42 with the expanded embolizing bodies or micropellets 12, whereby a substantially conformal embolizing implant 44 is formed that substantially fills the interior of the aneurysm 42. The micropellets 12, being mechanically attached to the carrier 14 and fixed in place thereon, stay attached to the carrier 14 during their expansion. Thus, the chance of a micropellet 12 separating from the carrier and migrating out of the vascular site is minimized.

It may be advantageous, prior to performing the procedural steps described above, preliminarily to visualize the aneurysm 42, by conventional means, to obtain a measurement (or at least an approximation) of its volume. Then, a device 10 of the appropriate size can be selected that would expand to fill the measured or estimated volume.

Although the device 10 has been described above for use in embolizing aneurysms, other applications will readily suggest themselves. For example, it can be used to treat a wide range of vascular anomalies, such as arteriovenous malformations and arteriovenous fistulas. Certain tumors may also be treated by the embolization of vascular spaces or other soft tissue voids using the present invention.

While a preferred embodiment of the invention has been described above, a number of variations and modifications may suggest themselves to those skilled in the pertinent arts. For example, the initial shape, size, and number of embolizing bodies 12 may be varied, as well as the length of the carrier 14. Furthermore, other mechanisms may be found for removable attaching the embolization device 10 to the deployment wire. One such alternative attachment mechanism may be a transition polymer joint that loosens when heated by contact with blood or by a low-level electric current. These and other variations and modifications are considered within the spirit and scope of the invention, as described in the claims that follow.

What is claimed is:

1. A device for embolizing a vascular site, comprising:
 an elongate, filamentous carrier formed of a flexible material having an elastic memory and initially configured with a portion forming a looped structure whereby the carrier assumes a three-dimensional shape; and a plurality of expansible embolizing elements non-releaseably carried on the carrier at spaced intervals along the length of the carrier within the portion forming the looped structure.

2. The device of claim 1, wherein the embolizing elements are formed of a hydrophilic hydrogel foam material.

3. The device of claim 2, wherein the foam material includes a water-swellable foam matrix formed as a macroporous solid comprising a foam stabilizing agent and a polymer or copolymer of a free radical polymerizable hydrophilic olefin monomer cross-linked with up to about 10% by weight of a multiolefin-functional cross-lining agent.

4. The device of claim 1, wherein the embolizing elements are formed of a material selected from the group consisting of polyvinyl alcohol foam, collagen foam, and poly (2-hydroxyethyl methacrylate).

5. The device of claim 1, wherein the embolizing elements are an initial diameter of not more than about 0.5 mm and are expansible to a diameter of at least about 3.0 mm.

6. The device of claim 1, wherein each of the embolizing elements has a predetermined initial volume and is expansible to an expanded volume that is at least 25 times its initial volume.

7. The device of claim 1, further comprising microcoil spacers located on the carrier between the expansible embolizing elements.

8. The device of claim 1, wherein the carrier includes a thin, flexible metal wire formed into a multi-looped configuration.

9. The device of claim 8, wherein the wire is made of an alloy of nickel and titanium that exhibits good elastic memory properties.

10. The device of claim 1, wherein the carrier includes a thin filament of polymer formed into a multi-looped configuration.

11. A method for embolizing a vascular site, comprising the steps of:

(a) passing a microcatheter intravascularly so that its distal end is in a vascular site;

(b) providing a vascular embolization device comprising a plurality of highly expansile embolizing elements carried on a flexible filamentous carrier initially configured with a portion forming a looped structure whereby the carrier assumes a three-dimensional shape, the embolizing elements being located at spaced intervals along the length of the carrier within the portion forming the looped structure;

(c) passing the embolization device through the microcatheter so that it emerges from the distal end of the microcatheter into the vascular site; and (d) expanding the embolizing elements in situ substantially to fill the vascular site with the embolizing elements and the carrier, while retaining the embolizing elements on the carrier.

12. The method of claim 11, wherein the step of providing a vascular embolization device includes the steps of:

(b)(1) determining at least the approximate volume of the vascular site; and (b)(2) selecting a vascular embolization device sized substantially to fill the entire volume of the vascular site after the expanding step.

13. The method of claim 12, wherein the step of determining at least the approximate volume of the vascular site includes the step of visualizing the vascular site prior to or during the step of passing the microcatheter intravascularly.

14. The method of claim 11, wherein the expanding step includes the step of passing saline solution through the microcatheter and into the vascular site.

15. The method of claim 11, wherein the step of passing the embolization device through the microcatheter includes the step of injecting a biocompatible, substantially non-aqueous fluid through the microcatheter to prevent the hydration of the expansible embolizing elements within the microcatheter.

16. The method of claim 15, wherein the substantially non-aqueous fluid is polyethylene glycol.

17. A device for embolizing a vascular site, comprising:

an elongate, filamentous carrier formed of a flexible material having an elastic memory and initially configured in a multi-loop configuration; and a plurality of expansible embolizing elements located at spaced intervals along the length of the carrier.

18. The device of claim 17, wherein the embolizing elements have a predetermined initial volume and are expansible to an expanded volume that is at least about 25 times their initial volume.

19. The device of claim 17, wherein the carrier has an intermediate portion on which the expansible embolizing elements are located, a proximal portion, and a distal portion.

20. The device of claim 19, wherein the intermediate portion is formed into at least one loop of approximately a first diameter, the proximal portion is formed into at least one loop of approximately the first diameter, and the distal portion is formed into at least one loop of approximately a second diameter that is greater than the first diameter.

21. The device of claim 19, further comprising an expansible linkage element on the proximal portion.

22. The device of claim 21, wherein the linkage elements are formed of the same material as are the embolizing elements.

23. The device of claim 17, wherein the embolizing elements are formed of a hydrophilic hydrogel foam material.

24. The device of claim 23, wherein the foam material includes a water-swellable foam matrix formed as a macroporous solid comprising a foam stabilizing agent and a polymer or copolymer of a free radical polymerizable hydrophilic olefin monomer cross-linked with up to about 10% by weight of a multiolefin-functional cross-linking agent.

25. The device of claim 17, wherein the embolizing elements are formed of a material selected from the group consisting of polyvinyl alcohol foam, collagen foam, and poly (2-hydroxyethyl methacrylate).

26. The device of claim 17, wherein the embolizing elements have an initial diameter of not more than about 0.5 mm and are expansible to a diameter of at least about 3.0 mm.

* * * * *